United States Patent [19]

Van der Knaap

[11] Patent Number: Plant 6,744

[45] Date of Patent: Apr. 18, 1989

[54] CHRYSANTHEMUM PLANT NAMED RHINO

[75] Inventor: Jacques C. M. Van der Knaap, De Lier, Netherlands

[73] Assignee: Fides Beheer B.V., De Lier, Netherlands

[21] Appl. No.: 124,991

[22] Filed: Nov. 23, 1987

[51] Int. Cl.[4] ..... A01H 5/00

[52] U.S. Cl. ..... Plt./74

[58] Field of Search ..... Plt./74

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A Chrysanthemum plant named Rhino, having flat capitulum form and single capitulum type, white ray florets, 70–80 mm diameter of inflorescence, and its vigorous growth habit.

1 Drawing Sheet

The present invention comprises a new and distinct cultivar of *Chrysanthemum morifolium*, hereinafter referred to by the cultivar name Rhino.

Rhino is a product of a planned breeding program which had the objective of creating new Chrysanthemum cultivars with single capitulum type, white ray florets, nine (9) weeks response, low temperature tolerance, and the ability to produce commercially acceptable quality in year around cut mum program. Such traits in combination were not present or needed improvement in previously available commercial cultivars.

Rhino was originated from a hybridization made by applicant in a controlled breeding program in De Lier, Holland in 1984. The female parent was Fanfare, an unpatented and non-commercial cultivar. The male parent of Rhino was Lucky Strike, a white daisy spray disclosed in a pending application of applicant.

Rhino was discovered and selected as one flowering plant within the progeny of the stated parentage by applicant in July 1984 in a controlled environment in De Lier, Holland.

The first act of asexual reproduction of Rhino was accomplished when vegetative cuttings were taken from the initial selection in September 1984 in a controlled environment in De Lier, Holland by a technician working under formulations established and supervised by applicant. Horticultural examination of selected units initiated in April 1985 has demonstrated that the combination of characteristics as herein disclosed for Rhino are firmly fixed and are retained through successive generations of asexual reproduction.

Rhino has not been observed under all possible environmental conditions. The phenotype may vary significantly with variations in environment such as temperature, light intensity, and day length. The following observations, measurements and comparisons describe plants grown in De Lier, Holland under greenhouse conditions which approximate those generally used in commercial practice.

The following traits have been repeatedly observed and are determined to be basic characteristics of Rhino, which in combination distinguish this Chrysanthemum as a new and distinct cultivar:

1. Flat capitulum form.
2. Single capitulum type.
3. Clear white ray florets.

4. Diameter across the face of the capitulum is 70–80 mm.
5. Yellow-green (immature) to yellow (mature) disc florets.
6. Vigorous growth habit.

Of the many commercial cultivars known to the present inventor, the most similar in comparison to Rhino is Cassa, an important commercial cultivar disclosed in a pending application of applicant. In comparison to Cassa, Rhino has more vigor, larger and darker green leaves, a larger flower diameter, true single disc center, and longer response time. The capitulum form, capitulum type, ray floret and disc floret colors are similar to those same characteristics of Cassa.

In comparision to the male parent Lucky Strike, which originated out of Cassa, Rhino has a true single disc center, less reflexing in the ray florets and somewhat wider ray florets.

The accompanying photographic drawing shows in side view typical inflorescence and foliage characteristics of Rhino, with colors being as nearly true as possible with illustrations of this type.

In the following description, color references are made to The Royal Horticultural Society Colour Chart. The color values were determined between 11:00 a.m. and 12:00 noon in June 1986 under natural daylight at De Lier, Holland.

Classification:

*Botanical.*—*Chrysanthemum morifolium*, Ramat., cv. Rhino.

*Commercial.*—Cut daisy spray.

INFLORESCENCE

A. Capitulum:

*Form.*—Flat.

*Type.*—Daisy.

*Diameter across face.*—70–80 mm.

B. Corolla of ray florets:

*Color (general tonality from a distance of three meters).*—White.

*Color (upper surface).*—155D.

C. Corolla of disc florets:

*Color (mature).*—Yellow.

*Color (immature).*—Yellow-green.

D. Reproductive organs:

*Androecium.*—Present only in disc florets; numerous.

*Gynoecium.*—Present in both disc and ray florets; numerous.

PLANT

A. General appearance:

*Height.*—85 cm.

B. Foliage:

*Color (upper surface).*—147A.

*Color (under surface).*—147B.

I claim:

1. A new and distinct cultivar of Chrysanthemum plant named Rhino, as described and illustrated, and parts thereof.

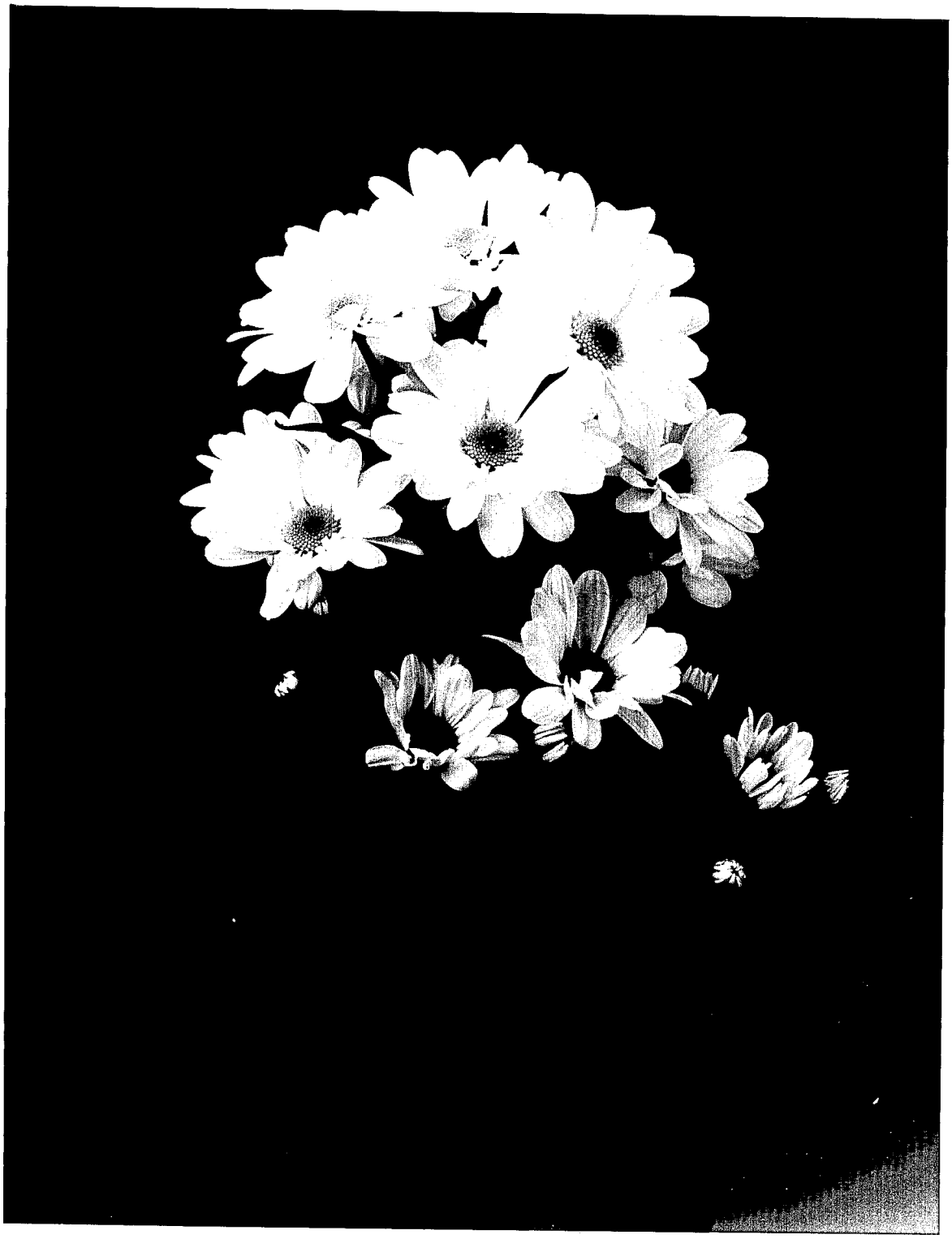

* * * * *